United States Patent [19]
Erickson

[11] Patent Number: 5,440,388
[45] Date of Patent: Aug. 8, 1995

[54] CHEMICAL ANALYSIS AND IMAGING BY DISCRETE FOURIER TRANSFORM SPECTROSCOPY

[76] Inventor: Jon W. Erickson, 3406 Rambow Dr., Palo Alto, Calif. 94306

[21] Appl. No.: 101,389

[22] Filed: Aug. 2, 1993

[51] Int. Cl.$^6$ ............................................. G01B 9/02
[52] U.S. Cl. .................................. 356/346; 356/345; 356/349
[58] Field of Search ...................... 356/345, 346, 349; 250/553, 578.1

[56] References Cited

U.S. PATENT DOCUMENTS

| | | | |
|---|---|---|---|
| 4,413,908 | 11/1983 | Abrams et al. | 356/346 |
| 4,905,169 | 2/1990 | Buican et al. | 356/346 |
| 5,021,661 | 6/1991 | Masutani | 356/346 |
| 5,076,699 | 12/1991 | Ryan et al. | 356/346 |
| 5,157,458 | 10/1992 | Wagner et al. | 356/346 |
| 5,257,086 | 10/1993 | Fateley et al. | 250/553 |
| 5,305,077 | 4/1994 | Grego et al. | 356/346 |

*Primary Examiner*—Samuel A. Turner
*Assistant Examiner*—Robert Kim
*Attorney, Agent, or Firm*—James J. Leary

[57] ABSTRACT

An instrument for chemical spectroscopy with imaging capabilities. A lightsource produces an array of light beams, each of which is made up of a plurality of discrete wavelengths. The array of light beams are modulated by an interferometer, then directed through a sample to an array of detectors. The sample may be a chemical mixture (e.g. a fuel stream in a manufacturing facility) or a body part (e.g. breast, limb, or head). An array of laser or light-emitting diodes provides light at the desired wavelengths and high intensity. The set of wavelengths is selected for a particular kind of analysis, and a specific set of possible absorbing species to be detected. The different wavelengths are guided optically (using fiber optics, lenses, and/or mirrors) into a single lightbeam, or an array of lightbeams. This light is then directed through the sample and onto a detector. The lightsource and detector, or lightsource alone, may be rastered if necessary to form an image. Individual lightbeams in an array may be modulated, polarized, or both so as to improve resolution. The signal from the detector undergoes a Fast Fourier Transform to produce a near-infrared absorption spectrum as a function of wavelength. The absorption spectra can be used to produce an image of the spacial distribution of detected species within the sample. Either the lightsource or detectors can be placed on the end of a probe or catheter for imaging through the wall of a hollow sample.

27 Claims, 7 Drawing Sheets

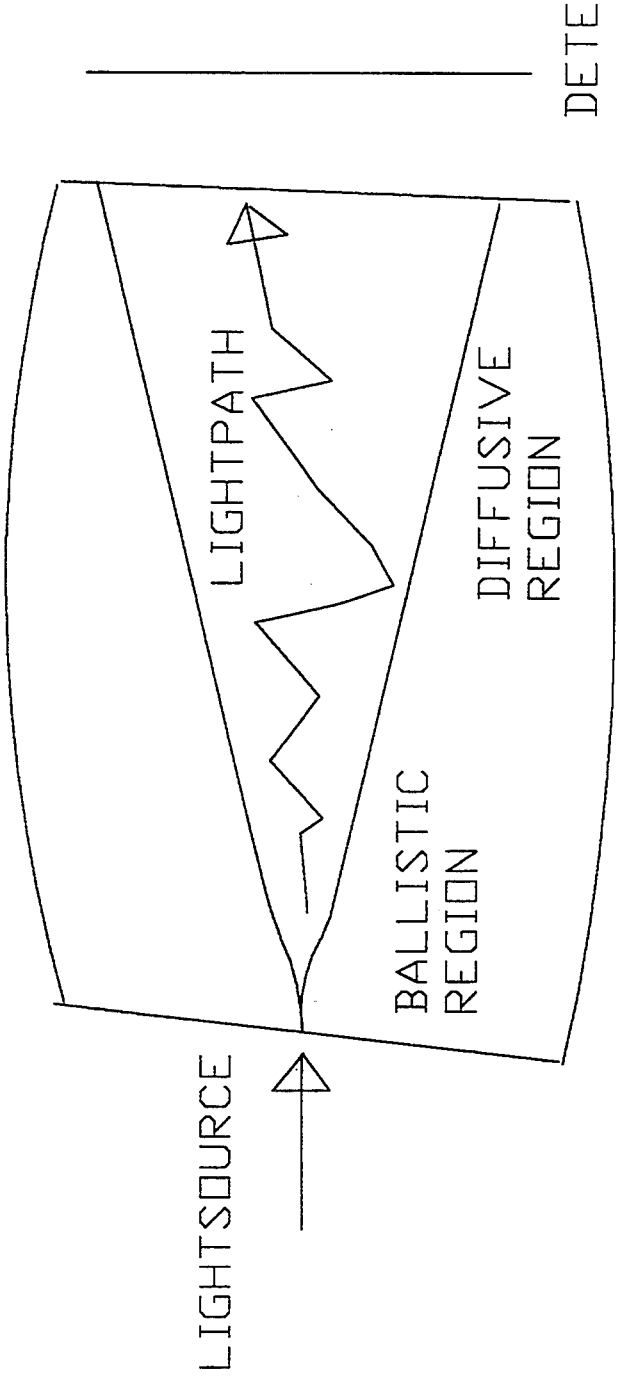
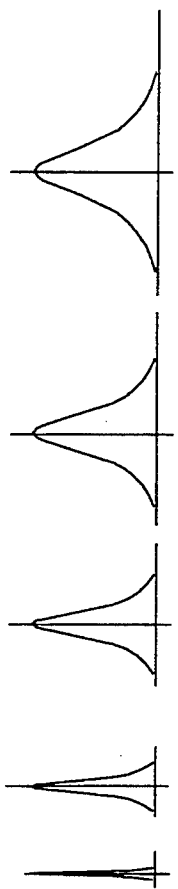
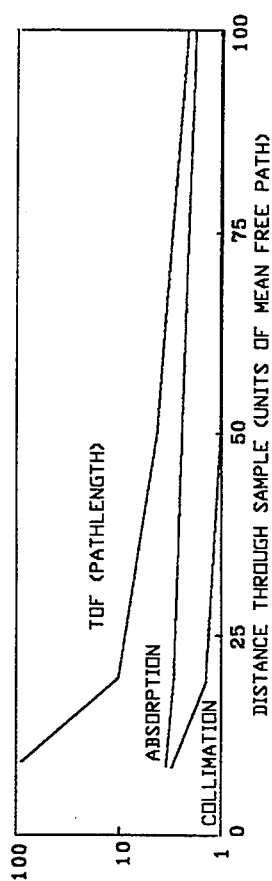
FIGURE 1A
FIGURE 1B
FIGURE 1C

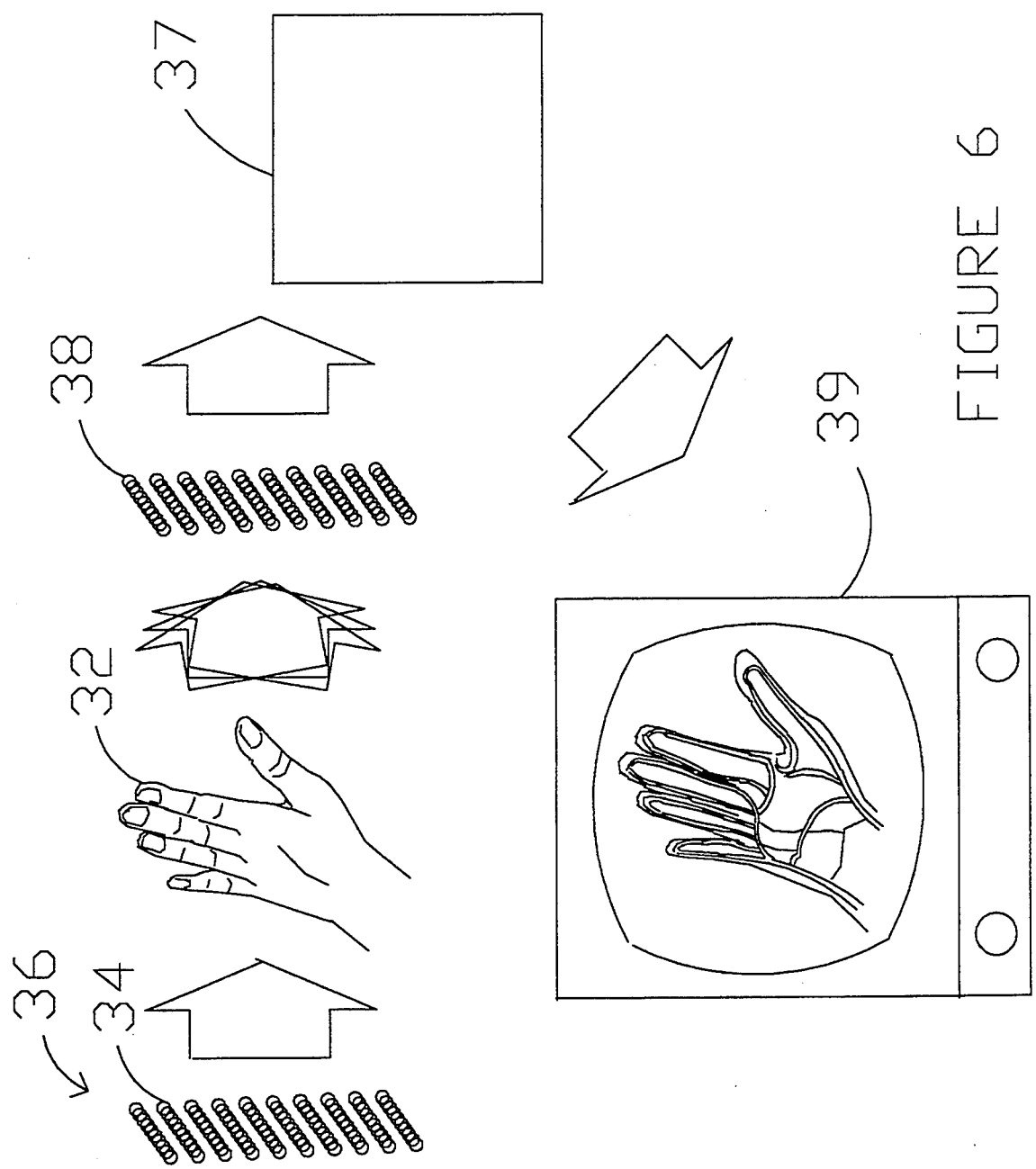

CHEMICAL ANALYSIS AND IMAGING BY DISCRETE FOURIER TRANSFORM SPECTROSCOPY

BACKGROUND OF THE INVENTION

1. Field of the Invention

The present invention relates to diagnostic medical instrumentation, or more generally to spectroscopic methods of analytical chemistry. In particular, the present invention defines a class of instruments which may be used to conveniently monitor various metabolites, or to quantitatively characterize the constituents of a chemical mixture. A primary objective of the present invention is to provide a versatile and relatively cheap spectroscopic device that can be used to determine the spatial distribution of such metabolites in a tissue, or components in a mixture.

2. Description of Background Art

The present invention concerns a novel design for a class of integrated optical devices. In brief the photons produced by a set of semiconductor light-emitting diodes (LEDs) or injection laser diodes (ILDs) are gathered into a small lightbeam or lightbeams. The wavelengths of light are chosen from the visible and infrared spectrum so as to permit the quantification of various components of a mixture through characteristic absorption behavior. Moreover the spatial distribution of these components may be determined in two dimensions so as to produce an image, by the manner in which the light is directed onto the sample and detected after it emerges from the sample.

The invention is described as "discrete" Fourier transform spectroscopy because discrete wavelengths are used rather than a continuum of light. The absorption spectrum is obtained by means of a Fourier transform.

The background an involves several distinct disciplines. Chemometry uses chemical measurements along with the statistical tools of multivariate calibration and analysis to quantify the components of a mixture. The chemical measurements can include near-infrared spectroscopy, which may be of a sort referred to as Fourier transform spectroscopy. Process analysis and control determine how chemical sensors can best be used to monitor industrial and other processes, while clinical chemistry identifies the manner in which chemometry may be usefully applied in medicine. Physical optics describes the various tools by which light can be analyzed and controlled, and the means to overcome certain experimental problems. Light-scattering in turbid samples is one such problem that has been addressed through various analytical models, experimental protocols, and image-processing techniques. Optoelectronics can produce monochromatic light of a desired wavelength at high efficiency, with semiconductor structures that can be mass-produced at low cost.

An imaging near infrared spectroscope could be used to analyze tissues and organs noninvasively, through the skin. Many chronic illnesses require invasive tests which withdraw blood for analysis, such as for glucose in the case of diabetes. Such blood tests are inconvenient and sometimes problematic. Simple applications of spectral analyses to such problems have appeared in the published literature, along with a variety of specific multivariate calibrations. However, any single scalar quantity such as a blood glucose level can probably be more economically and accurately determined by an implantable sensor designed for that specific purpose. Problems of biocompatibility will be overcome, so that implantable sensors seem to offer a more cost-effective means of monitoring such physiological parameters, while avoiding the painful and repetitive inconvenience of invasive blood tests. The most useful application of spectroscopy as a portable sensor technology seems to be in imaging samples: scanning the body (transillumination or diaphanography), or monitoring the spatial distributions of the components of a complex chemical mixture undergoing flow or other perturbations.

Chemometry applies mathematics and statistics as well as models of chemical structure to the quantitative analysis of chemical mixtures and solutions. Qualitative chemometric pattern-recognition techniques such as classification and clustering methods are applied to exploratory studies, while multivariate calibration is used for quantitative analyses of systems that are already relatively well-understood. The approach to calibration is empirical and condenses pertinent information into the most useful form, while structural models are used for both prediction and interpretation.

Multivariate calibration and analysis use statistical simplifications which have proved expedient to model and analyze complex chemical mixtures and solutions. Typically, the chemist starts by constructing a data matrix D from the spectra for a set of samples, and a control matrix C from a set of known concentrations. Then a suitable mathematical approach is chosen for reproducing the matrix D from the matrix C. Three common calibration methods include multiple linear regression (MLR), principal component regression (PCR) and partial least squares regression (PLSR).

MLR is adequate in ideal situations (linear and independent response of absorbing species, high dilution or no interactions of species, and low noise), but implicitly incorporates much irrelevant information into the model. MLR uses a linear combination of variables to solve the equation $C=AD+B$, where A is a matrix of coefficients estimated by linear regression, and B is a matrix of errors associated with (and minimized by) the MLR model. But real data includes much irrelevant or useless information which should not be given equal weight.

PCR explicitly deletes irrelevant noise and thereby reduces the dimensionality of the problem, which is helpful mathematically and practically in obtaining a solution. PCR is a factor-based modeling procedure, a factor being any linear combination of the original variables in C or R. Factors can be used to decrease the weighting given to irrelevant data, which can include redundant or collinear data as well as noise. PCR starts by determining the factors for the data matrix D, beginning with the linear combination or factor most correlated to the original variables, and proceeding to less and less correlated factors. The data matrix can then be re-expressed in terms of the factors as a score matrix F, in the process possibly deleting some factors and reducing the dimensions of the problem. Finally, MLR is used to solve the equation $C=AF$.

PLSR is also factor-based but further improves upon PCR by limiting the types of acceptable solutions to the problem. This is useful in obtaining a best fit to the data. The factors are determined for both the reference or control matrix C and the data matrix D at the same time. The factor model for PLSR thus is a compromise that describes both C and D, and incorporates more information in the model-building phase.

In practice for PCR or PLSR some optimal number of factors will exist which produces the best fit to the data. More factors than this optimal number will tend to decrease the predictive ability of the model, by over-weighting the effects of noise in the data. Fewer factors may ignore crucial features of the sample or relevant information.

(The particular wavelengths and factors best suited for a particular analysis would usually be identified through research and development, using a continuous spectrum. Neural nets implemented in hardware or software may help to identify more quickly the most significant wavelengths and best factors, for particular analytical problems. The set of wavelengths necessary for the analysis then could be implemented using discrete Fourier transform spectroscopy and imaging as described in the present invention.)

Near infrared spectroscopy (NIRS) is useful in examining aqueous solutions and mixtures, as well as in biological studies. While the chief application of absorption spectrometry is to quantitative measurements, such measurements are less sensitive in the infrared (IR) regime than in the visible or ultraviolet. This is because vibrational and other transitions responsible for infrared absorption are less intense than the electronic transitions in the visible and ultraviolet absorption. Consequently IR is not as sensitive in analyses of species present at low or trace concentrations. Yet electronic transitions have the drawback of often resulting in chemical changes, an undesirable side-effect when examining living tissue. The energy absorbed in vibrational transitions, however, is converted more directly into heat with less likelihood of harmful side-effects.

The less intense absorption of near-infrared wavelengths also allows them to penetrate sufficiently to be useful in the analysis of thicker samples, such as body tissues. Water, proteins, nucleic acids, and other molecules absorb strongly in the ultraviolet, visible, and mid-infrared region of the spectrum but only weakly in the near-infrared. Qualitative analysis in the IR regime is excellent, and very good quantitative results can be obtained for species present in moderate concentrations.

Beefs Law describes the nature of optical absorption in mixtures of linearly independent absorbing species:

$$I(z) = I_0 \exp(-NAd)$$

where $I_0$ is the incident light, N is the concentration of absorbers, A is the absorptivity, and d is the path length. For a mixture of j absorbing species, $$I(z) = I_0 \exp(-N_j A_j d)$$

where $N_j$ is the concentration of absorbers of the $j^{th}$ type, and $A_j$ is the absorptivity of the $j^{th}$ type. For the same mixture enclosed in a container with k absorbing barriers, $$I(z) = I_0 \exp(-N_j A_j d) + I_0 \exp(-n_k a_k)$$

where $N_k$ is the number of absorbing barriers of the $k^{th}$ type, and $A_k$ is the absorption of the $k^{th}$ type of barrier.

Beer's Law suggests a simple means of estimating constant absorption due to skin or other membranes in the light path. If the sample or tissue is compressed and released in order to alter its optical thickness d, constant contributions from less elastic parts or tissues may be subtracted from the absorption. This may help address problems such as differing levels of melanin in the skin, and better distinguish bone from fat. Also it is worth noting that the action of the heart introduces a natural frequency (the pulse) with which changes in blood pressure alter the amount of blood in the optical path. This can, for example, rhythmically change the concentration of oxygen by about 2%. Stroboscopic and schlieren methods can be used to select different parts of this cardiovascular cycle, or take difference measurements at the maximum and minimum blood pressures in order to better characterize the blood.

Differential photometry or the transmittance ratio method can be used to obtain better accuracy and precision at very low (or very high) concentrations. This involves the study of small changes in a predefined range of concentrations, seeking ways to amplify the effects of these changes and so boost the sensitivity of the measurement. A small range of concentrations is bracketed and a calibration curve is prepared using reference samples.

To the extent that the absorption behavior is linear, improved results may also be obtained by use of a dual-wavelength approach. Two wavelengths are chosen for each species-an isobestic point and a distinctive absorption peak. An isobestic point is a wavelength at which the system absorbance remains constant although the concentration of a given species is changing. An absorption peak often can be found that distinguish the species of interest; if necessary, more than one such peak and wavelength can be used per species. Thus at least two wavelengths, and possibly more, may be chosen for each species in the system. The use of multiple wavelengths per species also provides an important means to confirm the identification of a species to be quantified. For example, slight increases in temperature shift the water absorption bands to higher frequencies, lowering the transmission in at least one band of wavelengths useful for measuring glucose.

However, non-linearities are often present due to the interactions of various molecules and chemical or physical structures. Beefs Law does not fully describe many samples of interest, and multivariate calibration is required to predict and interpret the results. Moreover, samples which are relatively opaque or turbid may produce a great deal of light scattering, which further complicates analytical spectroscopy. The precise position of the spectrometer with respect to the sample can also introduce variations or changes in the data, which must be taken into account in the calibration algorithm.

The multivariate calibration method must take into account various other non-linearities that may be present in practice. These include high opacity or turbidity, due to scattering by the sample. Since instrumental noise becomes more significant in differential measurements, precautions must also be taken to optimize the signal-to-noise ratio. Despite all these complications, the measurement problem remains unchanged-the identification of the relative concentrations in a mixture.

Fourier transform spectroscopy has certain advantages over traditional spectroscopy, in which the response of a sample to light is measured by scanning sequentially over a range of wavelengths. Fourier transform spectroscopy measures the response of the sample to all the wavelengths of interest simultaneously, by measuring the light after it interacts with the sample and recording the entire spectrum at once. The signal is recorded as the Fourier transform of the wavelength, as a function of distance.

The Michelson interferometer is one of the simplest designs described in the prior art. A spectral interferogram is obtained with a Michelson interferometer by systematically varying the path length of one lightbeam with respect to a second lightbeam. The resolution (in wavenumbers or cm$^{-1}$) is defined by 1/d where d is the change in path length, while the sampling interval is $\frac{1}{2}$w where w is the maximum wavenumber of interest.

One advantage of Fourier transform spectroscopy is a better signal-to-noise (S/N) ratio. All X distinguishable wavelengths are measured simultaneously. Since the signal increases linearly and the noise with the square root of the measurement time, the S/N ratio increases by $X^{\frac{1}{2}}$ (the so-called Fellgett advantage). A suitable detector must be chosen, of course, so that the detector noise does not increase in proportion to the signal level.

Another advantage is that all the wavelengths are combined in a single beam of light, which can be adapted to microscopy and imaging applications.

The S/N ratio can be further improved by rejecting scattered or background light. Use of a single bandpass filter to filter out unwanted wavelengths in a continuous spectrum has been shown to decrease the root-mean-square noise level about 3-fold for a particular absorption band, with a more than 10-fold increase in sensitivity. Thus if FTIR measures only the wavelengths of interest, the dynamic range of the detector can be more fully utilized. A more efficient approach than filtering a continuous spectrum is taken in the present invention-only the wavelengths of interest for the analytical problem are generated.

Assume that a specific analytical problem requires a set of twenty or fewer wavelengths in the lightbeam. The spectral resolution requirements may not be very stringent to distinguish these discrete wavelengths from one another. If a resolution of 100 cm$^{-1}$ is sufficient, the path difference required is on the order of 1 millimeter. If the maximum wavenumber is 10,000 cm$^{-1}$ (a wavelength of about 1 micron), then the sampling interval is 0.5 micron and 2000 sampling intervals are required.

The digitized spectrum then can be processed with a "fast Fourier transform" or FFT algorithm. For a spectrum of N points FFT methods require about N*logN operations, whereas older matrix methods required N*N operations. The FFT works best when N is a power of 2, so that it is worthwhile to add null values to the spectrum to increase N until it is a power of 2 (otherwise the algorithm may work much more slowly). Thus a 2000-step spectrum should be increased to a 2048-step spectrum, and the FFT processing will be over 250 times faster than matrix methods.

Digital filtering also is of great use, in order to pass only that part of the signal that is at the frequencies or wavelengths of interest. It is generally desirable to remove from the data both high-frequency noise and low-frequency drift, or baseline variations. For the present invention, it would be desirable to pass only the frequencies corresponding to the original set of wavelengths. It is often more convenient (and faster) to filter in the Fourier domain, which simply involves multiplying the FFT by a filter function. One reasonable filter function is a set of Gaussian functions centered on the wavelengths of interest, with full-widths at half maxima corresponding to the linewidths of the lightsources.

The FFT of the signal on a detector produces a spectrum of intensity versus wavelength or frequency, from which absorption behavior can be obtained. This data is then evaluated with the PLSR calibration scheme, and the corresponding pixel in an image or display is colored so as to convey the pertinent information.

Process analysis and control is an important industrial and practical application of chemometry. Near-infrared wavelengths of light are absorbed due to distinctive molecular vibrations and low-level electronic excitations. Many molecules, particularly molecules of biochemical interest, have characteristic "fingerprint" absorption spectra in the near infrared. Consequently applications may exist for monitoring processes in biotechnology and diverse other industries. A common engineering problem in the mass production of a desired substance has to do with the dynamics of flow, or rheology. Remote or non-contact spectroscopic sensing avoids disruption of the flow patterns, while offering rapid feedback for process control.

Multivariate calibration methods can be adapted to statistical process control (SPC) techniques, which are in widespread use to maintain and improve product quality.

Clinical chemistry is another important practical application of chemometry. Clinical chemistry covers a very wide area, including the identification of cost-effective and reliable means of securing accurate diagnoses. (Appropriate regimes of therapy are chosen by other means.) Near infrared spectroscopy or NIRS was applied to human skin in the 1950's and has since been developed for transcutaneous measurements of body fat composition, oxygen levels in blood and tissue, and breast cancer screening as well as for many in vitro biochemical measurements.

Transillumination or diaphanography irradiates a body part such as the breast with near-infrared light, and records the image formed by transmitted light.

In traditional methods of transillumination, a broad lightbeam is directed into the body. Either reflected or transmitted light is used to project an image of internal body parts onto the skin. Light is reflected well from the interface of tissues with air or fluid so that this method has been used to image arteries and veins, seminal vesicles, intestines, and so forth. Other applications have been in specialties such as pediatrics of infants, ophthalmology, urology, venipuncture, and dentistry, which are not confronted with the problem of examining small organs deep within large bodies.

Radiologists have shown that transillumination can be used in mammography to distinguish benign tumors, malignant tumors, and cysts from each other. However, in clinical trials mammography using traditional methods of transillumination was no more effective then manual or physical examination, since the image resolution for transmitted light is limited to about 2 cm or so.

Image resolution can be improved using collimation and time-of-flight methods that have been recently developed for the examination of turbid samples.

In addition, near-infrared wavelengths penetrate biological tissues more deeply than visible light. Studies of brain function in fetuses and infants have used the absorption of infrared light to quantify levels of oxyhemoglobin, deoxyhemoglobin, and oxidized mitochondrial cytochrome oxidase. The concentrations of these molecules indicate cerebral blood flow and volume and change in response to external perturbations such as increased oxygen, the onset of contractions in labor, or the administration of various therapeutic drugs.

Physical optics concerns the properties of light and experimental means to generate, control, and measure light. This body of knowledge is necessary to the design of the present invention.

Optical coatings influence how much light is reflected, transmitted, or absorbed by each optical element in an instrument and so can help improve the overall performance. Anti-reflective coatings are suitable for prisms and lenses, while reflective coatings are desirable for mirrors and the cladding of fiberoptic lightguides. Coatings can form Fabry-Perot interference filters which transmit or reflect only desired wavelengths of light.

Spectrographs and spectrometers use prisms or gratings to disperse light according to wavelength. Spectrographs record the entire spectrum at once and spectrometers employ a slit to record only a narrow range of wavelengths at any given moment. A spectrograph can measure the absorption of all wavelengths in an infrared lightbeam simultaneously, but requires X detectors to record each of X separate wavelengths. Thus the S/N ratio decreases by $X^{0.5}$ compared to FTIR which uses a single detector. The number of optical components per lightbeam is also lower for FTIR, which therefore provides a more economical approach to imaging with arrays of lightbeams.

Materials for infrared optical applications are well-known. Metals or metallic coatings serve as good broadband infrared reflectors (with efficiencies on the order of 99%). Even higher reflectivities may be obtained over selected wavelength bands using all-dielectric or dielectric- enhanced-metal mirrors. Silica glass, aluminum oxide, and magnesium oxide transmit near-infrared light adequately. Germanium, germanium-arsenic-selenium glass, or arsenic trisulphide function well in the mid- and far-infrared regime. Infrared fiberoptics can be fabricated with chalcogenide glass (3-10 microns transmission), fluoride glass (0.5 to 4.3 microns), arsenic trisulphide (1 to 8 microns), AgClBr (3.3 to 15 micron), and sapphire (0.3 to 3.5 microns). Alternatively, hollow metal fibers can be effective broadband lightguides. Materials for lenses and prisms must be transparent in the spectral region of interest. The refractive index and spectral dispersion (rate of change in refractive index with wavelength) should both be large for a prism, while for a lens the spectral dispersion should be low to minimize chromatic aberration. For example, the angular dispersion is eight times lower for quartz than for heavy flint glass at a wavelength of 0.4 micron, making it a good choice for a lens but not a prism.

Mercury cadmium telluride (MCT) detectors are preferred for fast and sensitive infrared measurements. Both narrowband and wideband versions are available, the former having a cut-off at 750 cm$^{-1}$ and the latter at 400 cm$^{-1}$. Liquid nitrogen cooling is recommended for the best results, to reduce thermal noise to the background-limited infrared photodetector (BLIP) limit. (This limit decreases with decreasing wavelength and sample temperature; the infrared spectrum of a normal human being has a thermal maximum at a wavelength close to 10 microns.) A single liquid nitrogen reservoir may cool an array of MCT detectors. Detectors for spectroscopy in the visible to the very near infrared may be selected from a wide variety: photomultipliers, or semiconductor (Si, Ge or AlGaAsSb) photovoltaic or photoconductive designs. Photodiodes are photovoltaic or photoconductive designs operated at a large reverse-bias voltage, which offer high amplification and speed. Some Ge-based detectors are among the fastest broadband detectors, but do not reach as far into the IR as do HgCdTe detectors.

Optical multichannel analyzers (vidicons) use a silicon target with a microscopic array of up to 10,000,000 photodiodes to provide excellent spatial resolution. In combination with an image intensifier, a vidicon can provide quantum efficiencies on the order of 15%.

The image intensifier can also be gated in order to provide high time resolution. Optical, electo-optical, or electrical gating may be used either in the time domain or the frequency domain. Homodyne detection makes use of phase modulation and lock-in techniques, which are well-known and relatively easy to implement. (Heterodyne detection must deal with non-linear effects in somewhat sophisticated and expensive ways to attain good signal-to-noise ratios, but is less sensitive to imperfections and noise in the detector.) If an optical switch based on a Kerr or Pockels cell were used in front of the detectors to lock-in on a given phase, the dynamic range of the detector would be somewhat improved. An array of Kerr cells could be fabricated in the form of Ti-diffused $LiNbO_3$ channels. Whether the phase modulation takes place between the sample and detector, or after the detector, a single electronic phase-locked loop can be used to gate the entire array synchronously.

Light scattering occurs in turbid samples. When a lightbeam passes through a clear sample with negligible scattering, the photon trajectories are ballistic. A two-dimensional image maps directly onto its projection. The photon trajectory is no longer ballistic in a turbid sample, but diffuses away from the central axis of the trajectory as a result of multiple scattering events. The projection of an image will be blurred and attenuated, as indicated by the results of Monte Carlo simulations summarized in FIG. 1.

The trajectories through a sample can be described for photons of a given wavelength in terms of the mean free path and phase angle for scattering, and the mean free path for absorption. A given point in the original image will spread out onto a distribution of points in the projected image. In an isotropic sample, the diffusive spread can be described in terms of a Gaussian or normal distribution.

This Gaussian function is actually the product of several separate Gaussian distributions, each with its own characteristic halfwidth. The halfwidth is a quantity defined as half the width of the symmetric distribution, at a point that is half the maximum height or amplitude. The halfwidth for the product of two (or more) Gaussians is the sum of the individual halfwidths. It seems most instructive to conceive of the original image propagating through the sample, each point "blooming" or spreading according to the following distributions.

A. First, photons will tend to spread slightly from the axis due to divergence in the original lightbeam.
B. Second, scattering events will alter the exit angle or direction of the photons. Initially in the "ballistic" region the halfwidth of angles will be very small, but after many scattering events the halfwidth will become very large in a "diffusive" region.
C. Third, absorption will preferentially remove photons that are scattered far from the central axis or that have very long pathlengths. Absorptivities vary with wavelength, so this effect will also vary.

D. Fourth, the pathlengths or flight times of the photons have a characteristic distribution. The mean pathlength increases with the sample thickness.

E. If the original light was polarized, the degree of depolarization defines a fifth variable over which a distribution can be measured.

For extremely thick or turbid samples, all the halfwidths will be comparable to the sample size in which case no images can be resolved.

However in many practical cases the image resolution can be improved by selecting only the central portions of each of these distributions. This improves the spatial resolution of an image at the least cost in terms of the signal intensity or S/N ratio. The halfwidths for each distribution vary as a function of sample thickness (defined in units of the mean free path for scattering in FIG. 1). The mean free path for scattering is about 10–100 microns in biological tissues and bone, due in large pan to interactions with cells of size similar to the wavelengths of visible and near infrared light. (The mean free path for absorption is somewhat longer, especially in a spectral window of low absorption between 0.5 and 1.4 micron.)

In practice, how much can image resolution be improved by selecting the central portion of the "bloom"?

Image resolution better than 4 mm can probably be achieved for mammography in a direct imaging mode, scanning with a single lightbeam. Time-averaging and multiple lightbeams should permit even better resolution. Consider the following.

A. First, the position at which a photon exits the sample can be recorded precisely by use of apertures and a scanning detector or detector array. Traditional methods of medical transillumination illuminate the body with a broad beam of light, and inspect the distribution of light reflected from or transmitted through internal organs and tissues. The spatial resolution is limited to about 2 cm for a sample thickness of about 6–8 cm (e.g. mammography). Small veins near the surface of the skin can be imaged with better resolution-the worst case is for an object halfway through the sample for which no improvement can be obtained by reversing the direction of illumination.

B. Second, the angle at which a photon exits the sample can be selected by the use of two or more apertures placed in front of a detector to form a collimator. Collimation is used to discard light that has been scattered into directions far off-axis. Each scattering event usually changes a photon's direction only slightly. Collimation improves image resolution by recovering photons with ballistic trajectories, at the cost of much intensity. If a collimator accepts only light traveling within about 3 degrees of the original axis (a solid angle of about 0.01 steradian), well over 99% of diffuse light would be filtered out. Collimation has been used to achieve a resolution of about 1 mm in biological samples 3 cm thick, but about ten minutes were required to obtain sufficient signal to form an image. FIG. 1 suggests that collimation is most effective in thin samples for which ballistic photons are plentiful.

C. Third, the absorption of light will be greater for those photons which diffuse further outwards from the central axis and undergo longer trajectories. The graph in FIG. 1 indicates that discrimination by means of absorption is more effective than collimation in thicker samples. The absolute amount of absorption must be taken into account in the identification of the most suitable MLR protocol and factors for an analysis. If two absorption peaks are equally acceptable for quantitative analysis, then the one which rides on top of a broad absorption band might be preferable in order to improve the image resolution. But good contrast is necessary to achieve the best image quality, and may often impose the opposite choice D. Fourth, pathlength is a highly effective means of discriminating against off-axis photons. The shortest pathlength is just the thickness of the sample, for which the transit time is determined by the speed of light in the sample. Scattered and diffuse light will travel longer trajectories that take more time. The distance from the central axis increases as the square root of the pathlength or transit time, as expected for diffusion by means of a random walk. Shorter pathlengths can be selected by means of gating the signal for a very short interval on the time axis, or more cheaply by use of a modulated signal and a phase offset in the frequency domain to select the mean pathlength. The graph in FIG. 1 indicates that pathlength selection is the most effective means of improving image resolution. Modulation techniques are essential for chemical analysis as well, since accurate quantitative analysis in turbid solutions should ratio wavelengths of photons that have similar or identical pathlengths.

E. The fifth consideration mentioned was polarization, for which little relevant experimental dam is available. It seems reasonable to assume that light scattering will affect angles and polarization similarly, so that this will be of most use for ballistic rather than diffusive light.

How should the lightsource and detector be configured?

Three possible arrangements for imaging are as follows: rastering a single lightbeam in two dimensions, rastering a linear array of lightbeams in one dimension, or using a planar array of lightbeams with no rastering.

Rastering of a single lightbeam (e.g. in a left-to-right, top-to-bottom pattern like the electron beam in a television set) or a linear array (e.g. top-to-bottom only) may be accomplished in at least two ways. The first way is to actually move the lightsource or an optical aperture connected with fiberoptics to the lightsource, in a plane perpendicular to the direction of the light. The detector, or an optical aperture connected with fiberoptics to the detector, would then be moved synchronously in a second plane on the other side of the sample. A second, low-inertia way seems cheaper and quicker: use a set of stationary mirrors and lenses to amplify small motions of a directional mirror or a fiberoptic lightguide. Scanning with a directional mirror typically makes use of an oscillating plane minor, or a rotating mirror that is polygonal in cross-section and uses flat sides to sweep the beam across the sample. Two such directional mirrors would be necessary to scan a two-dimensional area. The detector could use a symmetric arrangement with a collimating aperture to ensure that only light from the proper location on the sample was collected.

However a typical image requires at least 100×100 pixels. The S/N for each pixel illuminated using a single beam would be 1% of the S/N obtained for a stationary beam. In addition, for Fourier transform interferometry the detector response time would have to be on the order of a nanosecond in order to collect 2000 increments of signal for each of 10,000 pixels every 1/30 second. Therefore any imaging method using a single beam cannot be used for real-time imaging of thick samples, but may suffice for slower acquisition of images from thin samples. For thicker samples and faster image acquisition, more light intensity and less rastering is necessary.

A $1\times 100$ linear array of lightbeams would require rastering or scanning in one dimension in order to form an image. It would yield 10% of the S/N of a stationary beam, and Fourier transform interferometry would require 100 nanosecond response time from a $1\times 100$ detector array.

A $100\times 100$ square array would require no rastering, would yield 100% of the S/N ratio of a stationary beam focused on one pixel, and requires only 10 microsecond response time for Fourier transform interferometry. The linear array might be cost effective for some samples, while square array seems the best choice for thick samples and fast or real-time imaging.

How should the center of the "bloom" be selected?

Image resolution is defined with respect to the photons of light, rather than the pixel-to-pixel separation which remains fixed during modulation. The resolution question is: With what probability can one determine the origin of a photon which arrives at a given detector. Only lateral resolution is considered here since axial resolution requires model-building, sample rotation, or other methods.

Assume that the lightbeams have Gaussian beam profiles with variance s in the plane of the detector, and travel along parallel axes that are located 2 s apart. Assume that the light is collected on a detector within a radius s about the axis of one lightbeam. For a linear array of lightbeams 2 s by 200 s in size, about 70% of the light will come from the lightbeam on that axis while about 30% of the light will be from nearest-neighbor lightbeams. For a square array 200 s by 200 s in size, about 45% of the light will come from the on-axis lightbeam and about 55% from the nearest and next-nearest neighbors. Thus it is necessary to find a way to discriminate against off-axis light, to trade some of the less informative signal for more resolution.

A. Positional Detection and Modulation

In an array of adjacent and parallel lightbeams, additional provisions for rejecting scattered light from adjacent sources may be convenient. Collimation cannot be carded to such an extreme as to filter out refracted as well as scattered light. One simple method is to modulate the signal from adjacent lightbeams, shutting off half the beams while the other half remain on.

Now, assume that alternating lightbeams are modulated with opposite duty cycles. A linear array . . . ABABAB. . . would be modulated so as to switch on first . . . A.A.A. . . while the B lightbeams were off, then to switch on . . . B.B.B. . . while the A lightbeams were off. In a linear array, this would mean that over 99% of the light comes from the on-axis beam, while less than 0.5% comes from next-nearest neighbors. The ratio of on-axis to neighboring light increases more than 100-fold to over 300, at a cost of half the signal or about 30% of the S/N ratio.

In a square array, alternating lightbeams are nearest-neighbors separated by 2 s, but the axes of the next-nearest neighbors are only about 2.8 s away. Shutting off the nearest neighbors will mean that about 70% of the light is from the on-axis lightbeam. The ratio of on-axis to stray light from other lightbeams increases more than 5-fold to about 2.3, at a cost of 50% of the signal and 30% of the S/N. If three sets of lights are defined so that both nearest-neighbors and next-nearest-neighbors are shut off, then the ratio of on-axis to stray light goes up to about 160. The improvement is at a cost of 70% of the signal, or about 50% of the S/N ratio. Clearly modulation can greatly enhance image resolution, at relatively low cost in terms of signal. Other geometries such as a hexagonal close-packed array will give somewhat different results, and the improvements may not be so dramatic for other choices of beam separation or Gaussian half-widths.

An adaptive modulation algorithm might be devised which selects the scheme best suited to the particular sample and analysis; the amount of scattering and refraction at different locations can be measured simply by turning a single lightbeam on at a time and measuring the signal on the detector array. Scattered light would of course be useful in determining average absorption values over the entire sample, providing the best S/N ratio without any concern for image resolution.

In general, image resolution is improved at the cost of signal. Thus the intensity, directionality, and mean free paths of the photons are key design parameters.

Semiconductor diode lasers are easily switched on and off, simply by adjusting the current supply. This has made them very useful in the digital transmission of information through fiberoptic communication cables. Addressable arrays of vertical cavity surface emitting laser (VCSEL) diodes have been fabricated, which might provide a relatively inexpensive means of chopping or modulating the signal according to some desired program or schedule.

An additional option is to polarize alternate lightbeams perpendicular to each other. Polarization filters usually cut the light intensity by more than 50%, but ILDs can be fabricated with strained active regions to increase the fraction of light that is polarized. This alternative seems expensive and limited in scope at present.

B. Collimation

For thin samples in which ballistic photons are still plentiful, some degree of collimation is beneficial. For thicker samples dominated by diffusive photons, collimation offers little or no advantage.

C. Absorption

The present invention is concerned with the chemical analysis of samples. In general the image of interest will be formed by the absorption of light by an object within the body, such as a vascularized tumor in the breast. Therefore, this particular means of improving resolution may only occasionally be practical. For example, if light of two wavelengths 0.9 and 1.3 microns were absorbed equally by the object of interest, but 0.9 micron light was absorbed better by the surrounding tissue, then the shorter wavelength might give a slightly better image. Such improvements are likely to be minor, however, and must be weighed against the loss of contrast. Image enhancement algorithms may of course make use of multiple wavelengths, some to maximize contrast and others to improve resolution.

D. Pathlengths

Selection of shorter pathlengths by means of time gating is relatively expensive and difficult to implement. However phase offset methods can provide a cost-effective means of selecting shorter pathlengths. Modulation has already been suggested as a means of improving positional resolution. If the light intensities are modulated at radio frequencies, then a lock-in or similar circuit can be used to detect the phase offset between the source and detector. The phase offset serves as a measure of the transit time. At a modulation frequency of 100 MHz, a phase offset of 1% would corresponds to a transit time lag of about 6 picoseconds. The mean phase difference corresponds to the mean transit time or pathlength, and will increase for thicker samples. If an optical switch is not used, the photodetector must have a very rapid response time in order to pass the high frequencies necessary for electronic modulation. Under some circumstances, heterodyne detection may be advantageous to improve the S/N ratio.

E. Polarization

As noted., this is probably analogous to angular collimation, and most effective in thin samples.

Is much image-processing or model-building necessary.

Since the mean free paths of scattering and absorption vary with wavelength, the images formed by photons of different wavelength will differ somewhat in resolution. For example near-infrared light has a longer mean free path of scattering than does green light in bone, fat, and blood.

The mean free paths also change with sample composition. For example, green light has a longer mean free path of absorption in fat than in blood (which therefore appears red).

For thick samples with diffusive propagation of light, selecting short pathlengths provides the best means of improving resolution. Different phase offsets might be used for different wavelengths, in order to obtain similar image resolution for all wavelengths. This would require small offsets of the duty cycles for each of the ILDs or LEDs. However, in practice it seems likely that any chromatic aberrations will be relatively minor.

More important perhaps is the need to make sure that quantitative analysis uses intensity ratios for photons that have indeed traversed comparable regions of the sample. Thus the pathlengths for photon wavelengths that are used in intensity ratios must be precisely selected.

Reconstruction of an image by means of modeling the sample may be useful in specific instances. For example, efforts to image the head may benefit from models that incorporate the characteristics of the layers of bone and tissue. Any detailed discussion of such models is outside the scope of the present invention.

The present invention requires considerable digital processing of the signal. For still images, the requirements are well within the capabilities of commercial digital video processor equipment. Real-time images of motion may be precluded simply by low signal intensities.

Optoelectronics is a field of solid state physics concerned with the design and fabrication of electronic materials which have desirable optical properties. An important category of optoelectronic materials are made of compound semiconductors such as AlAS, GaAs, InAs, GaP, InP, and various combinations thereof. Recent advances in materials science have drastically lowered the manufacturing costs for many optoelectronic devices. It appears possible to mass-produce optoelectronic devices that produce light of virtually any desired wavelength from the visible to the far infrared region of the spectrum. The bandwidth of light from injection laser diodes (ILDs) is much narrower than that from light-emitting diodes (LEDs). Fabry-Perot interference filters can be used to obtain quite narrow linewidths from LEDs, or even from the output of a continuous wave IR source after spectral dispersion by a prism or grating. Power considerations alone would seem to rule out the possibility of using a continuous-wavelength IR source, and selecting the photons with an array of Fabry-Perot interference filters, but LEDs might prove cost-effective. At present ILDs seem to offer the most efficient means of obtaining narrow linewidths, with good research prospects for new photonic technologies that increase conversion efficiency and decrease fabrication costs.

Various different semiconductor materials can be used in diode lasers to provide highly monochromatic photons across a range of wavelengths from 0.68 to 30 microns. The table below shows a representative list:

| Wavelength (micron) | Material |
|---|---|
| 0.68 to 1 | $In_{1-x}Ga_xP$ |
| 0.7 to 1 | $Al_xGa_{1-x}As$, $Ga_xAs_{1-x}P$ |
| 1 to 3.5 | $GaSb + In_xGa_{1-x}As$, $InAs_{1-x}P_x$ |
| 3.5 to 6 | $InAs_{1-x}Sb_x$ |
| 4.5 to 8 | $PbS_{1-x}Se_x$ |
| 7 to 30 | $Pb_{1-x}Sn_xTe$ |

Changes in the x value or mole fraction for the various compounds, alters the bandgap of the semiconductor and hence the wavelength of emitted light. It is necessary to characterize the spectral response and multivariate calibration scheme appropriate to the particular application, in order to best determine the number and value of wavelengths.

It is worth noting that the biological "window" for NIRS in biological tissue lies between 0.5 and 1.4 microns. The ILDs and LEDs that produce photons of these wavelengths are virtually commodity products, due to the great demand in other markets such as consumer electronics and communication fiberoptics. A MLR scheme that made use of wavelengths in this range would enjoy certain price advantages.

Other considerations involve the ease with which the materials can be grown by epitaxial means. The compounds of formula $Al_xGa_{1-x}As$ are relatively easy to grow, since the lattice constant does not change very much as a function of x and GaAs substrates can be used. Compounds of formula $In_{1-x}Ga_xAs_{1-y}P_y$ introduce another degree of freedom, so that the lattice constant and bandgap can both be chosen independently. For example, compositions that are lattice-matched to InP can be grown with wavelengths from 0.9 to 1.8 micron.

Further elaborations are possible such as using electric fields, magnetic fields, temperature control, nanostructural refinements and so on to tune the wavelengths of light and efficiency of conversion for a given compound. Two significant nanostructural tools are the use of microcavities to enhance stimulated emission, and electron mirrors to increase the efficiency of conversion. These techniques are part of the prior art or the subject of present research. Additional expense and complexity in the lightsource must be balanced against the increase in information content which can be obtained.

SUMMARY OF BACKGROUND ART

Much of the relevant prior art has been implemented in one form or another. Transillumination has been attempted so far with single beams and wavelengths, using time-gating to select shorter pathlengths. The improvements in image resolution have been impressive. Spectroscopic measurements of certain scalar quantities (total fat content, oxygen levels, and so on) have also been performed, with good results. The present invention is intended to provide spatially-resolved images of such quantities, at low cost.

The present invention is intended to provide a cost-effective, miniaturizable, and portable spectroscopy system that can be adapted to many different analyses. The design makes use of recent advances in electronic materials science and in chemometry, in order to provide the maximum useful information at the least cost. The set of wavelengths may be altered by substituting a different dime array, in order to better quantify or study different species.

SUMMARY OF THE INVENTION.

In accordance with the present invention, an instrument design is provided that offers chemical spectroscopy with imaging capabilities, at relatively low cost. The system comprises an external device which transmits light through a sample to an external detector. The sample may be a chemical mixture (e.g. a fuel stream in a manufacturing facility) or a body part (e.g. breast, limb, or head).

In the illustrative embodiments, an array of laser or light-emitting diodes provides a set of photons at desired wavelengths and high intensity. The set of wavelengths is selected with regard to a particular kind of analysis, and a specific set of possible absorbing species, in order to minimize the contributions of interferences or noise and to maximize the measurement reliability.

The different colors or wavelengths of photons are guided optically (using fiber optics, lenses, and/or mirrors) into a single lightbeam, or an array of lightbeams. The diameter or waist of a lightbeam would typically be several millimeters, but may be focused down to several microns if desired for purposes of microscopic examination, or defocused to increase the field of view for a given array or rastering geometry. This light is then directed through the sample and onto a suitable detector. The lightsource and detector, or lightsource alone, may be rastered if necessary to form an image. Individual lightbeams in an array may be modulated, polarized, or both so as to improve resolution.

The best material at present for an IR detector or array of detectors may be HgCdTe or Ge. The detector(s) may be cooled by thermal contact with a liquid nitrogen reservoir, in order to reduce thermal noise.

The signal from the detector undergoes a Fast Fourier Transform to produce a near-infrared absorption spectrum as a function of wavelength. The intensities of the discrete wavelengths can then be determined and solved for concentrations by multivariate calibration methods.

The development of a multivariate calibration algorithm involves first determining the model or set of factors that best relates a sample with reference data. Then this calibration algorithm must be validated in practice, to ensure that it is robust and not sensitive to noise or irrelevant information. Identifying the particular algorithms that are most suitable to the most common or important analytical problems is outside the scope of this invention. In both clinical and industrial applications, the present invention will work best within strict boundary conditions. A robust calibration scheme probably should be able to detect when boundary conditions have been violated, but it is important also to recognize the limitations of this analytical approach. It is easy to imagine ways to subtly alter the energy modes or vibrations of a sample, so that almost any calibration scheme becomes corrupt.

Both the FFT computation of the spectrum and its subsequent analysis by the method of factors used in PLSR can be implemented in very fast array processors, in order to produce and display images of concentration distributions in real time. Spatial averages of scalar values such as glucose, oxygen, and other baseline parameters may also be calculated, as may time-averages for individual pixels to increase the precision of information in the display.

A more detailed explanation of the invention is provided in the following descriptions and claims, and is illustrated in the accompanying drawings.

BRIEF DESCRIPTION OF THE DRAWINGS

FIGS. 1 A, B & C shows how light scattering degrades the spatial resolution of an image projected through a turbid sample.

FIG. 6 illustrates a process of scanning a body pan. The laser diodes are chosen to provide photons of wavelengths which are characteristically absorbed by oxyhemoglobin and skin, respectively. The distribution of oxyhemoglobin then may be displayed as a false-color map superimposed on the image of the hand.

DESCRIPTION OF THE PREFERRED EMBODIMENTS

FIG. 1A shows the manner in which light scattering affects an image projected through a turbid sample. Initially the photon trajectories are ballistic, but after multiple scattering takes place the trajectories can be described as diffusive. The light intensity is attenuated not only by scattering but also by absorption.

Once past the ballistic region, photon trajectories bloom outward from the central axis. The light diffuses outward at a constant rate, for a given distance along the axis. Thus a diffusive cone of light propagates through the sample for each original point. FIG. 1B shows the cross section of the diverging cone of light as it propagates through the sample.

Photons emerging from the other side of a turbid sample still may contain much information about the original image. This information is contained in the photon exit position, exit angle, absorption probability, and net pathlength. (If the original light was polarized, the residual polarization may also be of some use.) The distributions of each parameter can be used to improve the resolution of the projected image.

The image resolution can be improved by selecting only the central part of each distribution, especially of the pathlength distribution. This in effect selects only a narrow bloom, or amount of outward diffusion. FIG. 1C shows the resolution gain for 99% signal attenuation by three techniques. The graph shows that the pathlength distribution remains quite narrow compared to the other distributions, and offers the best increase in resolution in exchange for signal attenuation.

Figure 2:
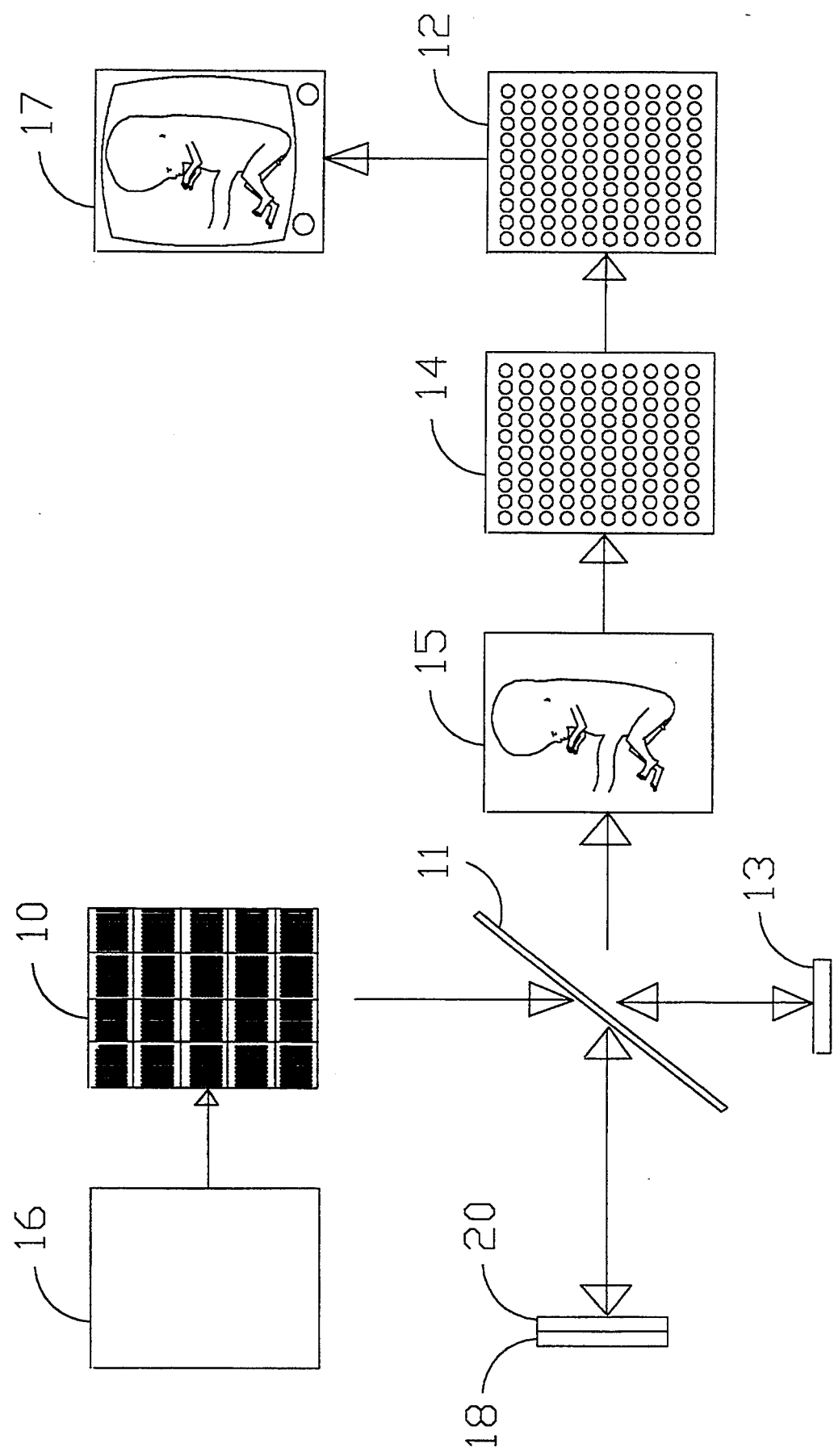
FIG. 2 is a block diagram of a FTIR scanning system constructed in accordance with the principles of the present invention.

FIG. 2 shows a scanning system constructed in accordance with the principles of the present invention. The lightsource 10, in this case an ILD array, and the detector 12 are depicted as square arrays that provide a square image. The detector arrays have very small acceptance apertures provided by a collimator or modulator 14, in order to discriminate against scattered light.

The lightsource 10 requires a controller 16, power 16, and possibly cooling until such time as very high efficiencies can be achieved with ILDs (perhaps using microcavities).

A piezoelectric assembly 18 can move the FTIR mirror 20 at 30 Hertz, since relatively small path differences must be achieved in precise increments. A stack of piezoelectric layers can be controlled in series, in order to use relatively low voltages to achieve net displacements on the order of a millimeter. Other mirrors 13, beam-splitters 11, lenses, and fiberoptic lightguides may be used as passive optical elements in the design. Ultimately, the information on the sample 15 is passed through signal processing 17 and the image shown on display 17.

Figure 3:
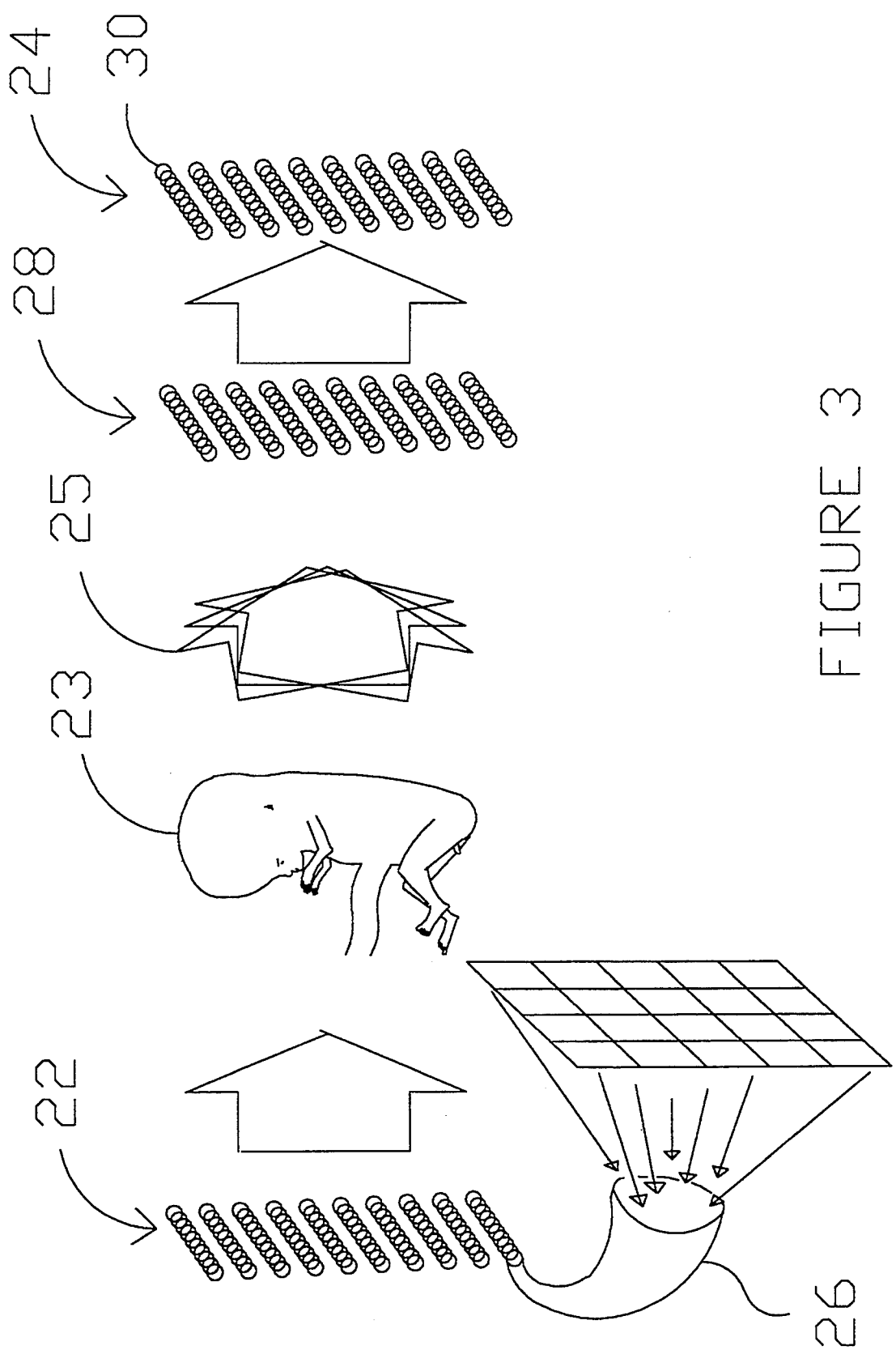
FIG. 3 illustrates different means for combining the output of individual ILDs into a multicolor lightbeam, and for using one or more lightbeams to scan an image along with a matched detector array.

FIG. 3 shows a matched lightsource 22 and detector array 24. A lightguide 26, either fiberoptic or hollow metal, is used to mix the colors from different types of ILDs into a multichromatic lightbeam with a relatively small divergence. Alternative schemes could use lenses, mirrors, or integrated fiberoptics for mixing if these prove less expensive.

A 100×100 array that uses 20 different colors would require 200,000 ILDs. The simplest approach at present to generating and mixing the photons seems to be to use 20 separate arrays of VCSEL diodes, each array producing one wavelength of photons. These vertically emitting diodes must be spaced sufficiently far apart to permit the emitted beams to be easily directed into specific lightguides. Microlenses or microlens arrays may be useful in reducing the divergence of emitted photons from each diode.

At present 32×32 addressable ILD arrays have been produced. With advances in photonics it may be possible to fabricate 100×100 arrays, or even arrays with 200,000 ILDs in which 100×100 sub-arrays of 20 different wavelengths are included. However, the simplest and cheapest approach may be to combine separate, monochromatic arrays of ILDs. Reliability issues are also significant-diodes are active elements with finite lifetimes or values for mean-time- between-failure (MTBF). Another alternative is to use linear arrays of more traditional side-emitting ILD structures. Square arrays can be fabricated by combining such linear arrays.

Suitable power, cooling, and control must also be provided to permit reliable operation.

In this example, twenty different wavelengths are assumed to be necessary to provide nine different PLSR factors for a particular analysis. The lightsource and detector arrays can be removed and replaced with new arrays with wavelengths better suited to other samples and analyses. The software algorithm used to modulate the lightbeams and to process the resulting data would also have to be changed, to match the new arrays.

The collimator or modulator 28 array directs light that has been transmitted through the sample 23, but not scattered 25, to the appropriate detector 30. Several parallel arrays of apertures may be used for this purpose, along with beamstops to minimize reflection and lenses to magnify dispersion.

Each detector 30 receives a FTIR signal, which must be converted with a FFT algorithm, evaluated for the intensities at the twenty wavelengths, and analyzed for concentrations with multivariate calibration. (The prior arts of software and hardware for rapid digital signal processing of large arrays of video data is already highly developed, and finds many applications in other fields.)

Figure 4:
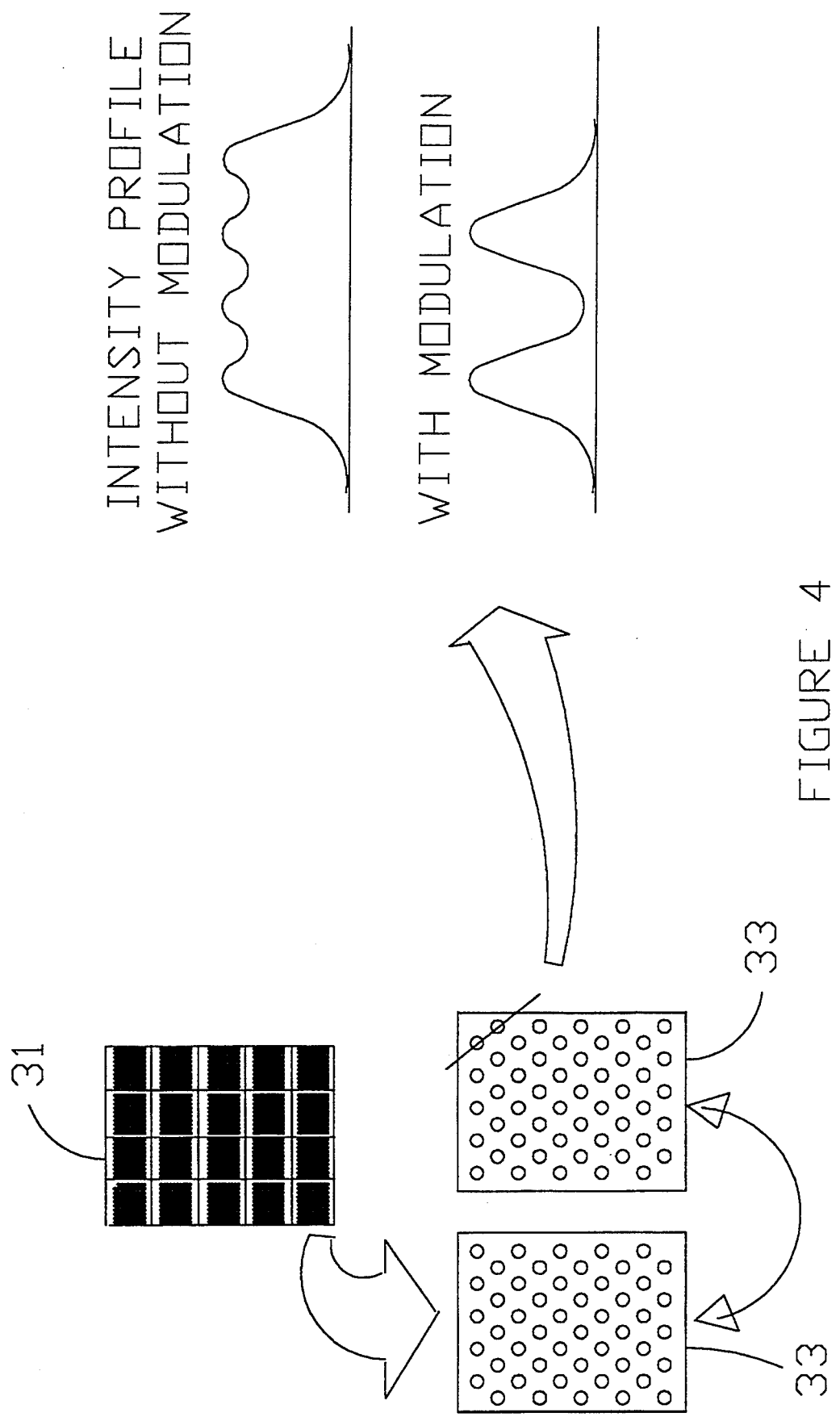
FIG. 4 illustrates optional interference filter(s), polarization filter(s), and beam chopping or modulation. These are common techniques to increase the signal-to-noise ratio at relatively low cost. Modulation appears to be the most effective general approach to discriminate against scattered and background light.

FIG. 4 shows the use of a modulation scheme to increase the image resolution, at the cost of a decrease in the signal-m-noise ratio. Either a linear array or a square array may be used, the linear array requiring a linear raster in order to obtain a two-dimensional image . In this case an ILD array 31 with 20 wavelengths, each with 100×100 ILD's is shown. Two individual arrays 33 are drawn as 10×10 arrays. A cross-section of the array 33 gives the intensity profile. The profile differs with modulation and without modulation. Modulation improves the peak-to-peak separation and the peak-to-valley difference in an intensity profile. The modulation scheme may be positional, pathlength-based, or both depending on the thickness of the sample and the degree of light-scattering. Positional modulation would involve switching neighboring lightbeams 33 on and off. Pathlength-based modulation would involve switching on and off or modulating each lightbeam, as well as gating the detector or sampling the detector signal with a small phase offset.

Figure 5:
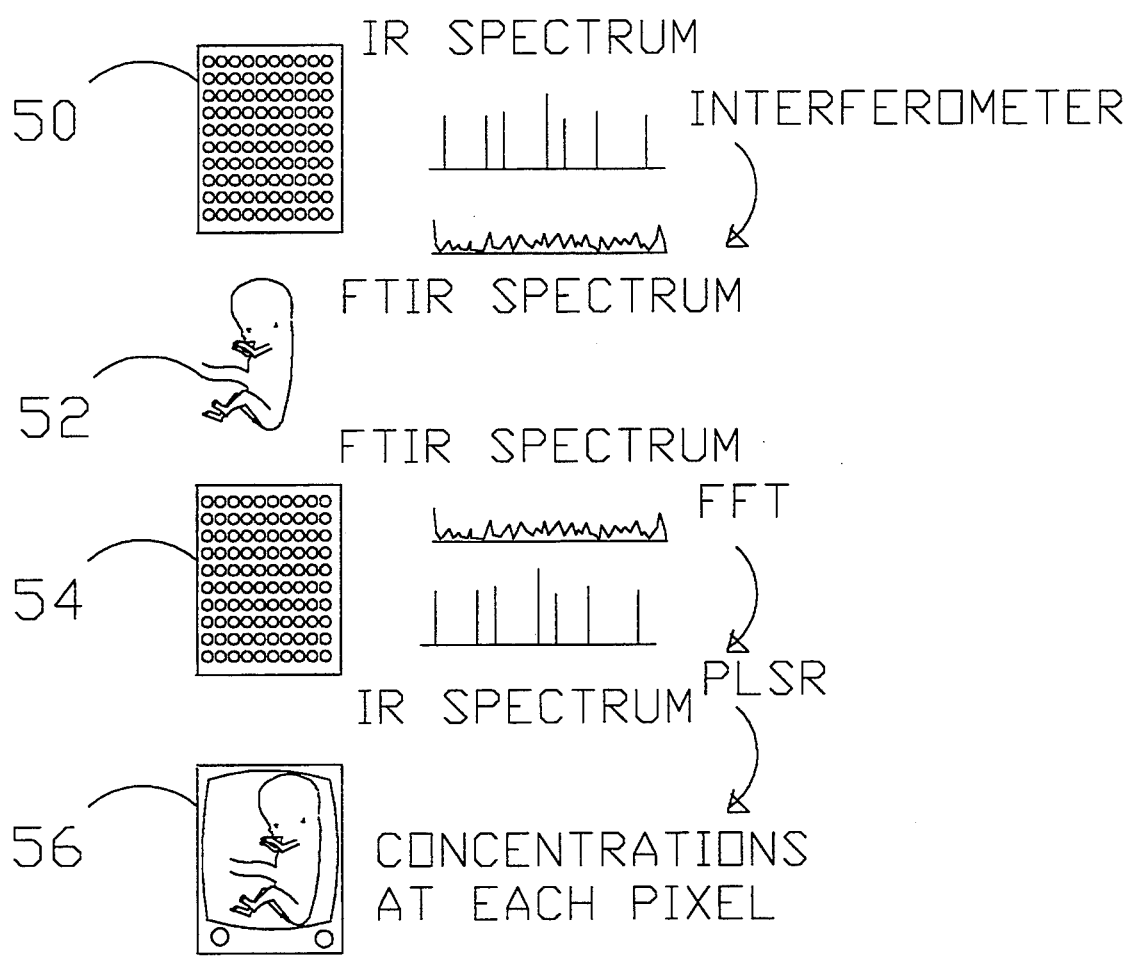
FIG. 5 illustrates the signal processing and algorithms by which a metabolite level may be identified. The specific algorithm appropriate to a particular analysis will determine the choice of light-emitting diodes and details of the matching detector array.

FIG. 5 graphically illustrates an algorithm for identifying a metabolite concentration. The specific algorithm for a given sample and kind of analysis determines the choice of wavelengths in the lightsource 50, shown here as an ILD array. The IR spectrum from the lightsource 50 is modulated by an interferometer to create an FTIR spectrum, which is passed through the sample 52. The FTIR spectrum of the light passing through the sample is received by the detector array 54 and the signal is subjected to a Fast Fourier Transfer analysis to obtain the IR spectrum. The IR spectrum is subjected to a PLSR analysis to determine the concentration of metabolites within each pixel of the sample 52, which is displayed as an image of the metabolite concentration on the display 56. The algorithm is represented in terms of vectors and matrices, corresponding to the PLSR factor, for the respective multivariate calibration.

The spectral information from the unknown and calibration samples is digitized to form the numerical matrices D and C. The matrix equation $D=CS+E$ then is solved using multivariate calibration analysis (such as the PLSR approach). Graphically, the column or row vectors of the matrix C are projected by multivariate regression onto those of the matrix D. The coefficients of the resultant matrix are the calculated concentrations of the metabolites at each pixel.

FIG. 6 illustrates a process of scanning a body part 32. The diodes 34 provide photons of wavelengths absorbed by oxyhemoglobin and skin. Concentrations would be displayed according to a color scheme which effectively presents the dam to the desired audience. For example, higher oxyhemoglobin concentrations might be shown in brighter shades of red, and lower in darker shades of blue, to communicate the connotations of arterial and venous blood. Such concentrations would be calculated from intensity ratios for a given pixel. Absolute intensities would denote the optical thickness of the sample and might be shown in shades of grey.

The scanning process illustrated here is a fast one, in which power and control are supplied to the interferometer and square lightsource 36 and, after passing through a collimator or modulator, detector arrays 38 are used to acquire the image with the best possible S/N ratio. This information is then processed by the FFT and digital array processors 37 to create an image of blood flow in the sample on display 39. Mirrors, beamsplitters, lenses, and fiberoptic lightguides may be used as passive optical elements if the design.

In order to permit real-time imaging, the S/N ratio must be sufficiently high to define a point or neighborhood on the calibration coordinates, for each pixel in the image every 0.03 seconds. Low concentrations or species that absorb light weakly may still require time-averaging for accurate and precise quantification, and thus might be displayed as running averages over longer time intervals.

Figure 7:
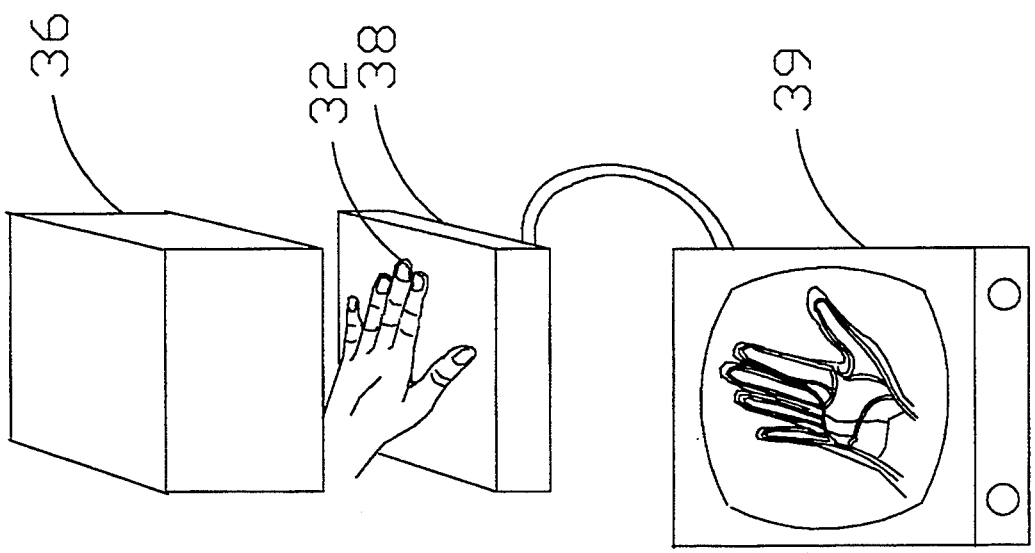
FIG. 7 illustrates one possible external appearance of the embodiment depicted in FIG. 6.

FIG. 7 illustrates one possible external appearance of the embodiment depicted in FIG. 6. The components of the invention are lightweight and compact, so that a practical embodiment may actually be portable.

Figure 8:
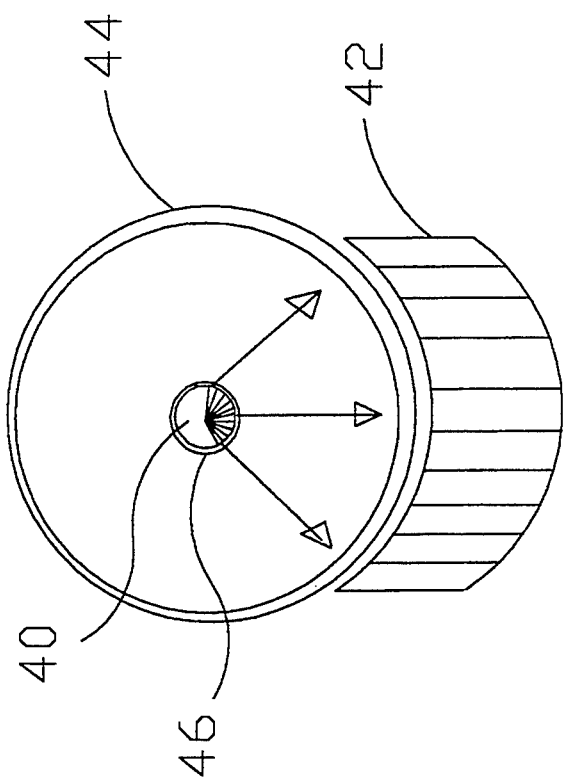
FIG. 8 illustrates an alternate embodiment for imaging hollow body structures.

FIG. 8 illustrates an alternate embodiment for imaging hollow body structures. The lightsource 40 is incorporated into a fiberoptic probe 46 or the body of an endoscope. The probe 46 with the lightsource 40 is inserted into a hollow body structure 44 or other sample with an internal cavity to illuminate the structure 44 from the inside. The detector 42 can be placed externally to the structure 44 for detecting the photons that pass through the structure 44. This embodiment may offer even greater resolution for imaging the walls of hollow organs or other structures by shortening the pathlength of the light and therefore the degree of scattering. In some applications it may be advantageous to reverse the positions of the lightsource 40 and the detector 42 such that the lightsource 40 is external and the detector 42 is internal to the sample 44. Also fiberoptic extensions of the lightsource 40 and the detector 42 might be used to permit endoscopy.

RAMIFICATIONS AND SCOPE

Perhaps the most widespread, immediate, practical application of the invention would be to mammography and to pediatrics. Three or four wavelengths should suffice to image vascularized tumors in both fatty and fibrous tissues, for example. Images with resolutions on the order of 1 mm probably can be obtained through collimation and pathlength selection. This roughly 10-fold improvement in spatial resolution opens up a very wide range of new applications (such as in obstetrics).

The present practice of mammography screening by x-rays makes use of ionizing radiation which is known to be carcinogenic, and may itself be responsible for about 0.2% of breast cancer. Similar concerns about cancer must be raised in pediatric situations (e.g. esolutions on the order of 1 mm probably can be obtained through collimation and pathlength selection. This roughly 10-fold improvement in spatial resolution opens up a very wide range of new applications (such as in obstetrics).

The present practice om mamography screening by x-rays makes use of ionizing radiation which is known to be carcinogenic, and may itself be responsible for about 0.2% of breast cancer. Similar concerns about cancer must be raised in pediatiric situations (e.g. in screening for bronchial pneumonia, a very common childhood occurrence).

Among existing non-invasive analytical techniques, only magnetic resonance imaging (MRI) offers a similar combination of chemical specificity and spatial resolution without ionizing radiation. Most of the components of the present invention are quickly becoming cheaper and more reliable, t a pace that is driven by related mass technologies (optical communication, photonic computing, and electro-optical devices). It seems very unlikely that MRI machines will become affordable in price or compact in size (e.g. potable or even desk-top analytical units) in the near future, whereas the present invention offers exactly this prospect in the near term.

Geometric Arrangements

The illustrative embodiments have shown scanning protocols in which the lightsource and detector are rastered in parallel planes in order to obtain spatially-resolved distributions of concentration in two dimensions. Many other geometries are possible, and may be better suited to particular measurements or samples.

These methods may be extended to three dimensions for tomography of internal structures or to obtain solid models of molecular distributions, for example by rotating the sample about an axis perpendicular to the direction of the transmitted lightbeams. In addition, more finely focused beams may be used for microscopy, and more defocused beams may be used to obtain larger fields of view. Triangulation might be used to better image objects deep within the sample. Finally, signals in thin samples may be sufficiently intense to obtain data with sufficient rapidity to display real-time images.

Improvements in Related Technology

Several possible ILD arrays have been described. The use of integrated lightguides on a planar surface is another possible arrangement, in which silica or other materials are deposited in such a way as to channel and multiplex light from several individual ILD emitters to a single output port or lens. Such planar monolithic technology for photonics is possible, but higher packing densities require higher conversion efficiencies and lower power consumption. A single ILD typically consumes more than 10 mW of power at present and have efficiencies no greater than 10%. The ideal of direct conversion would be to produce little or no thermal energy.

The prices of optoelectronic components and of computer processors are likely to continue decreasing in the future, making an optimized design for transillumination an increasingly cost-effective analytical method. Further research in the field of chemometry will provide additional algorithms and candidates for analysis by near-infrared spectroscopy. Thus the present invention should continue to be a useful and versatile tool.

Value Versus Cost in the Frequency and Time Domains

Four frequencies are fundamental to this invention: that of the light wavelengths, the modulation frequency, the interferometer cycling frequency, and the frequency at which a useful image can be formed.

The frequency of light with wavelengths from 1 to 10 microns is about $10^{15}$ to $10^{16}$ Hz. The modulation frequency is necessarily in the $10^8$ to $10^9$ Hz region, in order to measure changes in phase. The interferometer may cycle at $10^2$ Hz or less, slower rates enjoying more time averaging but susceptible to greater 1/f noise. The rate at which useful images can be formed depends on the sample thickness.

In thin samples, it might be useful to introduce a fifth frequency-modulation of the lightbeam at the same frequency as some time-variant process in the sample in Schlieren and stroboscopic methods of measurement. One of the more noticeable biological frequencies suited to NIRS is that of the pulse. Thus it may be possible to locate and resolve aneurysms or other dynamic cardiovascular anomalies even in thick samples, by time-averaging a strobed image.

Due to the long exposure times required for the best results, flexible designs with fiberoptics could be used to minimize discomfort. This would compare favorably with present methods that use uncomfortable compression protocols and seek to minimize net exposure. A small lightsource array or detector array could also be used to advantage in endoscopy, to provide better resolution with a relatively non-invasive procedure.

Value Versus Cost in the Energy and Spatial Domains

Past in vivo applications of transillumination have included dentistry, laparoscopy, opthalmology, pediatrics, and veterinary medicine. For very thin biological samples in which ballistic photons remain plentiful, it might be possible to acquire images in real-time.

Increased spatial resolution requires higher total doses. Near-infrared photons pose less of a hazard than higher energy photons or ionizing radiation, since the main effect is heating of the sample. Skin bums have reportedly been the main hazard associated with traditional methods of laparoscopy. The rate of power absorption is much more significant than the total dose. In many cases, moreover, most of the absorption will occur before the light has penetrated halfway through the sample. This suggests that some advantages in the form of more uniform heat-dissipation (and higher acceptable light intensities) might be realized in a three-dimension scanning arrangement in which the lightsource/detector rotates about the sample.

It also seems possible to use image-enhancement algorithms, so that the signal from all wavelengths is combined to provide the best net spatial resolution. Thus 16 wavelengths give a 4fold increase in S/N for resolution. Application of stroboscopic techniques also can be used to improve spatial resolution, by allowing better focus and the application of time-averaging to features that otherwise would change at the pulse rate.

Miscellaneous Applications

Polarized light and polarization filters can also be used to measure phenomena such as optical rotation, fluorescence depolarization, and so on. These may require single wavelengths and different geometries (e.g. a detector array facing the sample but at right angles to the transmitted light).

Many other spectroscopic and scanning techniques are part of the prior art, and may be adapted to the present invention in order to better measure particular samples or phenomena. The increased resolution and chemical specificity offered by the present invention suggests a wide range of new applications.

Although the illustrative embodiments show several examples of this invention, it is to be understood that various modifications and substitutions for the illustrative diodes, optical guides, filters, and detectors may be made by those skilled in the relevant art without departing from the novel spirit and scope of the present invention.

What is claimed is:

1. An optical sensor comprising:
   a plurality of monochromatic lightsources, each of said monochromatic lightsources producing light at a discrete wavelength, means for combining the light from said plurality of monochromatic lightsources into at least one light beam, said at least one light beam comprising a plurality of discrete wavelengths of light,
   an interferometer means for modulating said at least one light beam from said light source,
   means for directing said at least one light beam through a sample,
   a detector having means for detecting each of said plurality of discrete wavelengths of light in said at least one light beam after said at least one light beam has passed through said sample, said detector producing a detector signal indicative of the intensity of each of said plurality of discrete wavelengths of light in the detected light beam,
   and a signal processing means for analyzing said detector signal.

2. The optical sensor of claim 1 wherein said signal processing means performs a Fourier transform on said detector signal.

3. The optical sensor of claim 1 wherein said signal processing means performs a fast Fourier transform on said detector signal.

4. The optical sensor of claim 1 wherein said interferometer means comprises a beam splitter which splits said at least one light beam into a first light path and a second light path, said first light path having a fixed pathlength, said second light path having a pathlength which is varied cyclically, and a means for recombining said first light path and said second light path.

5. The optical sensor of claim 1 wherein said signal processing means analyzes the composition of said sample based on the absorption of each of said plurality of discrete wavelengths of light in said at least one light beam by said sample.

6. The optical sensor of claim 1 wherein said means for combining the light from said plurality of monochromatic lightsources into at least one light beam Combines the light from said plurality of monochromatic lightsources to produce a two dimensional array of light beams, each of the light beams in said two dimensional array of light beams comprising a plurality of discrete wavelengths of light.

7. The optical sensor of claim 6 wherein said signal processing means forms an image of said sample based on the absorption of each of said plurality of discrete . . . . .wavelengths of light in each of the light beams in said two dimensional array of light beams by said Sample.

8. The optical sensor of claim 6 wherein said signal processing means analyzes the composition of said sample based on the absorption of each of said plurality of discrete wavelengths of light in each of the light beam in said two dimensional array of light beams by said sample and forms an image representing the distribution of the composition of said sample.

9. The optical sensor of claim 6 wherein said means for combining the light from said plurality of monochromatic lightsources produces said two dimensional array of light beams by combining the light from said plurality of monochromatic lightsources into a single light beam comprising a plurality of discrete wavelengths of light and rastering said single light beam in two dimensions.

10. The optical sensor of claim 6 wherein said means for combining the light from said plurality of monochromatic lightsources produces said two dimensional array of light beams by combining the light from said plurality of monochromatic lightsources into linear array of light beams, each of the light beams in said linear array of light beams comprising a plurality of discrete wavelengths of light and rastering said linear array of light beams in one dimension.

11. The optical sensor of claim 6 further comprising a modulation means for improving the signal-to-noise ratio of said optical sensor wherein said modulation means comprises a means for selecting photon from said at least one light beam having the shortest, direct pathlength from said lightsource means from said detector means and for rejecting photons having a longer, less direct pathlength from said lightsource means to said detector means.

12. The optical sensor of claim 6 further comprising a modulation means for improving the signal-to-noise ratio of said optical sensor wherein said modulation means comprises a means for selecting photons from said at least one light beam having a given pathlength from said lightsource means to said detector means.

13. The optical sensor of claim 12 wherein said modulation means comprises a phase locked loop for selecting photons from said at least one light beam having a given pathlength from said lightsource means to said detector means.

14. The optical sensor of claim 12 wherein said modulation means comprises a gating circuit for selecting photons from said at least one light beam having a given pathlength from said lightsource means to said detector means.

15. The optical sensor of claim 1 further comprising a collimator for eliminating scattered and off-axis light from said at least one light beam after it has passed through said sample and before it is detected by said detector means.

16. The optical sensor of claim 1 wherein said sample comprises a biological tissue.

17. The optical sensor of claim 16 further comprising a compression means for compressing said biological tissue to alter the pathlength of said at least one light beam through said biological tissue.

18. The optical sensor of claim 16 wherein said optical sensor analyzes metabolites within said biological tissue.

19. The optical sensor of claim 1 wherein said means for directing said at least one light beam through a sample comprises a plurality of fiber-optic waveguides mounted on an elongated probe means for insertion into a hollow sample and means for directing light transmitted by said plurality of fiber-optic waveguides through a wall of said hollow sample, said mean for combining the light from said plurality of monochromatic lightsources into at least one light beam comprising means for combining the light from said plurality of monochromatic lightsources into a plurality of lightbeams and means for directing each of said plurality of light beams into a separate fiber-optic wave guide in said plurality of fiber-optic waveguides, each of said plurality of light beams comprising a plurality of discrete wavelengths of light, and said detector being configured to detect the light transmitted through said wall of said hollow sample from said plurality of fiber-optic waveguide.

20. An optical sensor comprising:
a plurality of monochromatic lightsource each of said monochromatic lightsources producing light at a discrete wavelength, means for combining the light from said plurality of monochromatic light sources into a two dimensional array of light beams, each of the light beams in said two dimensional array of light beams comprising a plurality of discrete wavelengths of light,
an interferometer means for modulating said array of light beams from said light source,
means for directing said array of light beams through a sample,
a detector having means for detecting each of said plurality of discrete wavelengths of light in said array of light beams after said array of light beams has passed through said sample, said detector comprising a two dimensional array of broadband light detectors, said detector producing a detector signal indicative of the intensity of each of said plurality of discrete wavelengths of light in the detected array of light beams,
and a signal processing means for analyzing said detector signal.

21. The optical sensor of claim 20 wherein said signal processing means analyzes the composition of said sample based on the absorption of each of said plurality of discrete wavelengths of light in said array of light beams by said sample and forms an image representing the distribution of the composition of said sample.

22. The optical sensor of claim 20 further comprising a switching means for improving the signal-to-noise ratio of said optical sensor, said switching means dividing said light beams of said two dimensional array into at least two groups and activating said at least two groups alternately.

23. The optical sensor of claim 22 wherein said switching means divides said light beams of said two dimensional array into two groups such that light beams which are nearest neighbors in said two dimensional array are in different groups and activating said two groups alternately.

24. The optical sensor of claim 22 wherein said switching means divides said light beams of said two dimensional array into three groups such that light beams which are nearest neighbors and which are next nearest neighbors in said two dimensional array are in different groups and activating said three groups alternately.

25. The optical sensor of claim 20 wherein at least one of said means for directing said array of light beams through a sample or said detector means is mounted on an elongated probe means for insertion into a hollow sample and wherein said means for directing said array of light beams through a sample directs said array of light beams through a wall of said hollow sample.

26. An optical sensor comprising:
a plurality of monochromatic lightsources, each of said monochromatic lightsources producing light at a discrete wavelength, means for combining the light from said plurality of monochromatic light-sources into a linear array of light beams, each of the light beams in said linear array of light beams comprising a plurality of discrete wavelengths of light, an interferometer means for modulating said linear array of light beams from said light source, means for directing said linear array of light beams through a sample, a detector having means for detecting each of said plurality of discrete wavelengths of light in said linear array of light beams after said linear array of light beams has passed through said sample, said detector producing a detector signal indicative of the intensity of each of said plurality of discrete wavelengths of light in the detected light beam, and a signal processing means for analyzing said detector signal.

27. The optical sensor of claim 26 wherein at least one of said means for directing said linear array of light beams through a sample or said detector is mounted on an elongated probe means for insertion into a hollow sample and wherein said means for directing said linear array of light beams through a sample directs said linear array of light beams through a wall of said hollow sample.

* * * * *